(12) United States Patent
Vilarino et al.

(10) Patent No.: US 8,335,362 B2
(45) Date of Patent: Dec. 18, 2012

(54) DEVICE, SYSTEM AND METHOD FOR MEASUREMENT AND ANALYSIS OF CONTRACTILE ACTIVITY

(75) Inventors: Fernando Vilarino, Lugo (ES); Panagiota Spyridonos, Patras (GR); Petia Radeva, Barcelona (ES); Jordi Vitria, Barcelona (ES); Fernando Azpiroz, Barcelona (ES); Juan Malagelada, Barcelona (ES)

(73) Assignee: Given Imaging Ltd., Yoqneam (IL)

( * ) Notice: Subject to any disclaimer, the term of this patent is extended or adjusted under 35 U.S.C. 154(b) by 605 days.

(21) Appl. No.: 12/304,526

(22) PCT Filed: Jun. 12, 2007

(86) PCT No.: PCT/IL2007/000709
§ 371 (c)(1),
(2), (4) Date: Apr. 22, 2009

(87) PCT Pub. No.: WO2007/144879
PCT Pub. Date: Dec. 21, 2007

(65) Prior Publication Data
US 2009/0202117 A1    Aug. 13, 2009

Related U.S. Application Data

(60) Provisional application No. 60/812,629, filed on Jun. 12, 2006.

(51) Int. Cl.
*G06K 9/00* (2006.01)
*A61B 1/04* (2006.01)

(52) U.S. Cl. .................. 382/128; 382/276; 600/117

(58) Field of Classification Search .................. 382/128, 382/107, 276, 286
See application file for complete search history.

(56) References Cited

U.S. PATENT DOCUMENTS

| 4,278,077 A | 7/1981 | Mizumoto |
| 5,005,559 A | 4/1991 | Blanco et al. |
| 5,604,531 A | 2/1997 | Iddan et al. |
| 5,957,833 A | 9/1999 | Shan |
| 5,993,378 A | 11/1999 | Lemelson |
| 6,050,960 A | 4/2000 | Ferzli |
| 6,095,989 A | 8/2000 | Hay et al. |
| 6,240,312 B1 | 5/2001 | Alfano et al. |
| 6,428,469 B1 | 8/2002 | Iddan et al. |
| 6,459,919 B1 | 10/2002 | Lys et al. |

(Continued)

FOREIGN PATENT DOCUMENTS
EP    1997076    12/2008
(Continued)

OTHER PUBLICATIONS

Office Action for U.S. Appl. No. 10/097,096 mailed on Aug. 11, 2004.

(Continued)

*Primary Examiner* — Tony Ko
(74) *Attorney, Agent, or Firm* — Pearl Cohen Zedek Latzer, LLP (57) ABSTRACT

A method and system for determining intestinal dysfunction condition are provided by classifying and analyzing image frames captured in-vivo. The method and system also relate to the detection of contractile activity in intestinal tracts, to automatic detection of video image frames taken in the gastrointestinal tract including contractile activity, and more particularly to measurement and analysis of contractile activity of the GI tract based on image intensity of in vivo image data.

14 Claims, 6 Drawing Sheets

U.S. PATENT DOCUMENTS

| | | | |
|---|---|---|---|
| 6,632,175 | B1 | 10/2003 | Marshall |
| 6,709,387 | B1 | 3/2004 | Glukhovsky et al. |
| 6,764,440 | B2 | 7/2004 | Iddan et al. |
| 6,944,316 | B2 * | 9/2005 | Glukhovsky et al. ......... 382/107 |
| 7,009,634 | B2 | 3/2006 | Iddan et al. |
| 7,039,453 | B2 | 5/2006 | Mullick et al. |
| 7,231,062 | B2 | 6/2007 | Zhang et al. |
| 7,319,781 | B2 | 1/2008 | Chen et al. |
| 7,869,856 | B2 | 1/2011 | Refael |
| 8,022,979 | B2 | 9/2011 | Miyamoto et al. |
| 8,139,859 | B2 | 3/2012 | Kruger et al. |
| 2002/0042562 | A1 | 4/2002 | Meron et al. |
| 2002/0103417 | A1 | 8/2002 | Gazdzinski |
| 2002/0109774 | A1 | 8/2002 | Meron et al. |
| 2002/0111544 | A1 | 8/2002 | Iddan |
| 2002/0173718 | A1 | 11/2002 | Frisch et al. |
| 2002/0177779 | A1 | 11/2002 | Adler et al. |
| 2003/0190064 | A1 | 10/2003 | Inoue |
| 2004/0204630 | A1 | 10/2004 | Gilad |
| 2005/0075537 | A1 | 4/2005 | Chen et al. |
| 2006/0069317 | A1 | 3/2006 | Horn et al. |
| 2006/0193505 | A1 | 8/2006 | Glukhovsky et al. |
| 2006/0222249 | A1 | 10/2006 | Hosaka et al. |
| 2007/0060798 | A1 | 3/2007 | Krupnik et al. |
| 2007/0076930 | A1 | 4/2007 | Zinaty et al. |
| 2007/0078300 | A1 | 4/2007 | Zinaty et al. |
| 2007/0188604 | A1 | 8/2007 | Miyamoto et al. |
| 2008/0119691 | A1 | 5/2008 | Yagi et al. |
| 2009/0284589 | A1 | 11/2009 | Radeva et al. |
| 2010/0080460 | A1 | 4/2010 | Kruger et al. |
| 2011/0044515 | A1 | 2/2011 | Spyridonos et al. |

FOREIGN PATENT DOCUMENTS

| | | |
|---|---|---|
| JP | 10 014864 | 1/1998 |
| JP | 2002 336193 | 11/2002 |
| WO | WO 00/22975 | 4/2000 |
| WO | WO 01/06926 | 2/2001 |
| WO | WO 2007/105214 | 9/2007 |

OTHER PUBLICATIONS

Final Office Action for U.S. Appl. No. 10/097,096 mailed on Feb. 24, 2005.

Office Action for U.S. Appl. No. 10/097,096 mailed on Aug. 11, 2005.

Final Office Action for U.S. Appl. No. 10/097,096 mailed on Apr. 7, 2006.

Office Action for U.S. Appl. No. 10/097,096 mailed on Aug. 24, 2006.

Final Office Action for U.S. Appl. No. 10/097,096 mailed on Sep. 4, 2007.

Office Action for U.S. Appl. No. 10/097,096 mailed on Nov. 23, 2007.

Office Action for U.S. Appl. No. 10/097,096 mailed on Jun. 5, 2008.

Hirata et al., Study of New Prognostic Factors of Esophageal Variceal Rupture by Use of Image Processing With a Video Endoscope, Surgery, pp. 8-16, 1994.

Ichikawa et al., Quantitative analysis of red color sign in the endoscopic evaluation of esophageal varices, Endoscopy, vol. 33, Issue No. 9, pp. 747-753, 2001.

Final Office Action for U.S. Appl. No. 10/097,096 mailed on Mar. 30, 2009.

Office Action for U.S. Appl. No. 10/747,371 mailed on Jul. 13, 2005.

Final Office Action for U.S. Appl. No. 10/747,371 mailed on Mar. 1, 2006.

Office Action for U.S. Appl. No. 10/747,371 mailed on Jun. 23, 2006.

Final Office Action for U.S. Appl. No. 10/747,371 mailed on Oct. 13, 2006.

Office Action for U.S. Appl. No. 10/747,371 mailed on Feb. 21, 2007.

Final Office Action for U.S. Application No. 10/747,371 mailed on Aug. 24, 2007.

Medscape Gastroenterology, "A Mosaic Pattern of the Descending Duodenum", Medscape Gastroenterology, vol. 2, Issue No. 1, 2000. Medscape, <URL: http://www.medscape.com/viewarticle/405488_2>, Retrieved: Jun. 2, 2008.

Office Action for U.S. Appl. No. 11/235,541 mailed on Sep. 8, 2008.

Final Office Action for U.S. Appl. No. 11/235,541 mailed on Feb. 25, 2009.

Tjoa, M.P. et al., "Feature extraction for the analysis of colon status from the endoscopic images", Biomed Eng. Online 2003, vol. 2, Issue No. 9, Apr. 8, 2003.

Kang, J. et al., "Real-time image processing system for endoscopic applications", Electrical and Computer Engineering, 2003, IEEE CCECE 2003. Canadian Conference on May 4-7, 2003, vol. 3, pp. 1469-1472.

Chindaro et al., "Colour space fusion for texture recognition", Video/Image Processing and Multimedia Communications, 2003, 4$^{th}$ EURASIP Conference focused on Jul. 2-5, 2003, vol. 1, pp. 181-186.

Office Action for U.S. Appl. No. 11/239,208 mailed on Aug. 16, 2007.

Final Office Action for U.S. Appl. No. 11/239,208 mailed on Dec. 27, 2007.

Office Action for U.S. Appl. No. 11/239,208 mailed on Jan. 27, 2009.

Office Action for U.S. Appl. No. 11/358,292 mailed on Aug. 17, 2007.

Final Office Action for U.S. Appl. No. 11/358,292 mailed on Dec. 28, 2007.

Office Action for U.S. Appl. No. 11/358,292 mailed on Oct. 29, 2008.

Igual et al., "Eigenmotion Extraction for Characterization of Intestinal Motility, Research", Lecture Notes in Computer Science, vol. 4673, pp. 293-300, 2007.

Vilarino, Fernando, "A Machine Learning Approach for Intestinal Motility Assessment with Capsule Endoscopy", Dissertation, Universitat Autonoma de Barcelona, pp. 1-179, Jun. 12, 2006.

Spyridonos et al., "Anisotropic Feature Extraction from Endoluminal Images for Detection of Intestinal Contractions", Medical Image Computing and Computer-Assisted Intervention—MIC CAI, 2006 Lecture Notes in Computer Science, vol. 4191, pp. 161-168, Oct. 1-6, 2006.

Vilarino et al., "Linear Radial Patterns Characterization for Automatic Detection of Tonic Intestinal Contractions", Progress in Pattern Recognition, Image Analysis and Applications Lecture Notes in Computer Science, vol. 4225, pp. 178-187, Nov. 14-17, 2006.

Spyridonos et al., "Identification of Intestinal Motility Events of Capsule Endoscopy Video Analysis", Advanced Concepts for Intelligent Vision Systems Lecture Notes in Computer Science, vol. 3708, pp. 531-537, Sep. 20-23, 2005.

Vilarino et al., "ROC curves and video analysis optimization in intestinal capsule endoscopy", Pattern Recognition Letters, vol. 27, No. 8, pp. 875-881, Jan. 19, 2006.

Vilarino et al., "Experiments with SVM and Stratified Sampling with an Imbalanced Problem: Detection of Intestinal Contractions", Pattern Recognition and Image Analysis Lecture Notes in Computer Science, vol. 3687, pp. 783-791, Jan. 1, 2005.

Vilarino et al., "Self Organized Maps for Intestinal Contractions Categorization with Wireless Capsule Video Endoscopy", 3$^{rd}$ European Medical and Biological Engineering Conference, EMBEC'05, IFMBE, pp. 1-15, Nov. 20-25.

Hwang et al., "Automatic Measurement of Quality Metrics for Colonoscopy Videos", 13$^{th}$ Annual ACM International Conference on Multimedia, pp. 912-921, Nov. 6-11, 2005.

Mackiewicz et al., "Colour and Texture Based Gastrointestinal Tissue Discrimination", Acoustics, Speech and Signal Processing, 2006. ICASSP 2006 Proceedings, 2006 IEEE International Conference on Toulouse, pp. II, May 14-19, 2006.

Yu et al., "A Visual Model Approach for Parking Colonoscopy Videos", Image and Video Retrieval; Lecture Notes in Computer Science, vol. 3115, pp. 160-169, Jun. 25, 2004.

An Yong et al., "Informative Frame Filtering in Endoscopy Videos", Proceedings of SPIE, vol. 5747, pp. 291-302, Feb. 12-17, 2005.

Oh, Jungwan, "Blurry Frame Detection and Shot Segmentation in Colonoscopy Videos", Proceedings of SPIE, vol. 5307, pp. 531-542, Jan. 20-22, 2004.

Berens et al., "Stomach, Intestine and Colon Tissue Discriminators for Wireless Capsule Endoscopy Images", Proceedings of Spie, vol. 5747, pp. 283-290, Feb. 12-17, 2005.

Vilarino, "Automatic Detection of Intestinal Juices in Wireless Capsule Video Endoscopy", ICPR 2006, IEEE, pp. 179-722, Aug. 20-24, 2006.

Supplementary European Search Report for European Application No. EP 07736449 dated Dec. 18, 2009.

Supplementary European Search Report for European Application No. EP 07713343 dated Dec. 22, 2009.

Office Action issued by the United States Patent and Trademark Office for U.S. Appl. No. 12/282,700 dated Aug. 13, 2012.

* cited by examiner

DEVICE, SYSTEM AND METHOD FOR MEASUREMENT AND ANALYSIS OF CONTRACTILE ACTIVITY

CROSS-REFERENCE TO RELATED APPLICATIONS

This application is a National Phase Application of PCT International Application No. PCT/IL2007/000709, International Filing Date Jun. 12, 2007, which claimed priority from U.S. Provisional Patent Application No. 60/812,629, filed Jun. 12, 2006, which is hereby incorporated by reference.

FIELD OF THE INVENTION

The present invention relates to the field of in-vivo sensing, and more particularly to the field of in-vivo imaging.

BACKGROUND OF THE INVENTION

Peristalsis within a gastro-intestinal (GI) tract may transport swallowed food and may aid in digestion and eventual evacuation. Peristalsis may result in pressure waves or contractions moving along the GI tract, thereby resulting in motility of a bolus or other object within the GI tract.

Certain pathological conditions may alter the normal motility within the GI tract. Low motility may be caused by, for example, an obstruction, a blockage, or other pathological condition. Motility disorders may be caused by, for example, nervous disorders, and may not necessarily be visible.

Some in-vivo sensing systems may include an in-vivo imaging device able to acquire and transmit images of, for example, the GI tract while the in-vivo imaging device passes through the GI lumen.

Other devices, systems and methods for in-vivo sensing of passages or cavities within a body, and for sensing and gathering information (e.g., image information, pH information, temperature information, electrical impedance information, pressure information, etc.), are known in the art.

SUMMARY OF THE INVENTION

Some embodiments of the invention may include, for example, devices, systems, and methods for measurement and analysis of contractions and/or contractile activity of the GI tract.

Some embodiments may include, for example, a system having a processor to detect, determine, measure, calculate and/or analyze contractions and/or contractile activity within a body lumen based on analysis of data received from an in-vivo device.

Some embodiments may include, for example, a system having a processor to automatically diagnose intestinal dysfunctions, such as intestinal dysmotility, based on measurement and analysis of contractions and/or contractile activity within the GI tract by analysis of data received from an in-vivo device.

Some embodiments may include, for example, determining contractions and/or contractile activity based on brightness, darkness and/or image intensity of multiple in-vivo images. For example, in some embodiments, a gradual increase and decrease in image intensity across a series of nine consecutive in-vivo images may be use to determine a contraction.

Some embodiments may include, for example, determining contractions and/or contractile activity based on identification of phasic contractions, which may be detected as luminal occlusion and characterized by wall texture analysis.

Some embodiments may include, for example, determining non-contractile patterns which may be detected by La Placean filtering, and may be identified as wall or tunnel appearance.

In some embodiments, values related to following features may be used in the diagnosis of intestinal motility dysfunctions: static frames, turbid frames, tunnel frames and/or wrinkle pattern level presence.

In some embodiments, an in-vivo device may include, for example, an in-vivo imaging device, an in-vivo sensing device, an autonomous in-vivo device, and/or a swallowable capsule.

Embodiments of the invention may provide various other benefits or advantages.

BRIEF DESCRIPTION OF THE DRAWINGS

The subject matter regarded as the invention is particularly pointed out and distinctly claimed in the concluding portion of the specification. The invention, however, both as to organization and method of operation, together with containers, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth hi order to provide a thorough understanding of the invention. However, it will be understood by those skilled in the art that the present invention may be practiced without these specific details. In other instances, well-known methods, procedures, components and circuits have not been described in detail so as not to obscure the present invention.

Although a portion of the discussion may relate to in-vivo imaging devices, systems, and methods, the present invention is not limited in this regard, and embodiments of the present invention may be used in conjunction with various other in-vivo sensing devices, systems, and methods. For example, some embodiments of the invention may be used, for example, in conjunction with in-vivo sensing of pH, in-vivo sensing of temperature, in-vivo sensing of pressure, in-vivo sensing of electrical impedance, in-vivo detection of a substance or a material, in-vivo detection of a medical condition or a pathology, in-vivo acquisition or analysis of data, and/or various other in-vivo sensing devices, systems, and methods.

Some embodiments of the present invention are directed to a typically one time use or partially single use detection and/or analysis device. Some embodiments are directed to a typically swallowable in-vivo device that may passively or actively progress through a body lumen, e.g., the gastrointestinal (GI) tract, for example, pushed along by natural peristalsis. Some embodiments are directed to in-vivo sensing devices that may be passed through other body lumens, for example, through blood vessels, the reproductive tract, urinary tract, or the like. The in-vivo device may be, for example, a sensing device, an imaging device, a diagnostic device, a detection device, an analysis device, a therapeutic device, or a combination thereof. In some embodiments, the in-vivo device may include an image sensor or an imager. Other sensors may be included, for example, a pH sensor, a temperature sensor, a pressure sensor, sensors of other in-vivo parameters, sensors of various in-vivo substances or compounds, or the like.

Devices, systems and methods according to some embodiments of the present invention, including for example in-vivo sensing devices, receiving systems and/or display systems, may be similar to embodiments described in U.S. Pat. No. 5,604,531 to Iddan et al., entitled "In-vivo Video Camera System", and/or in U.S. Pat. No. 7,009,634, entitled "Device for In-Vivo Imaging", issued on Mar. 7, 2006, and/or in U.S. patent application Ser. No. 10/046,541, entitled "System and Method for Wide Field Imaging of Body Lumens", filed on Jan. 16, 2002, published on Aug. 15, 2002 as United States Patent Application Publication Number 2002/0109774, and/or in U.S. patent application Ser. No. 10/046,540, entitled "System and Method for Determining In-vivo Body Lumen Conditions", filed on Jan. 16, 2002, published on Aug. 15, 2002 as United States Patent Application Publication Number 2002/0111544, and/or in U.S. patent application Ser. No. 11/226,350, entitled "System and Method for Presentation of Data Streams", filed on Sep. 15, 2005, and/or PCT Patent Application Number PCT/IL2007/000322, entitled "Device, System and Method for Automatic Detection of Contractile Activity in an Image Frame", filed on Mar. 13, 2007, and/or PCT Patent Application Number PCT/IL2007/000323, entitled "Cascade Analysis for Intestinal contraction Detection", filed on Mar. 13, 2007, all of which are hereby incorporated by reference in their entirety. Devices and systems as described herein may have other configurations and/or sets of components. For example, an external receiver/recorder unit, a processor and a monitor, e.g., in a workstation, such as those described in one or more of the above publications, may be suitable for use with some embodiments of the present invention. Some embodiments of the present invention, for example, may be practiced using an endoscope, a needle, a stent, a catheter, or other suitable devices. Some in-vivo devices may be capsule shaped, or may have other shapes, for example, a peanut shape or tubular, spherical, conical, or other suitable shapes.

Some embodiments of the present invention may include, for example, a typically swallowable in-vivo device. In other embodiments, an in-vivo device need not be swallowable and/or autonomous, and may have other shapes or configurations. Some embodiments may be used in various body lumens, for example, the GI tract, blood vessels, the urinary tract, the reproductive tract, or the like. In some embodiments, the in-vivo device may optionally include a sensor, an imager, and/or other suitable components.

Embodiments of the in-vivo device are typically autonomous and are typically self-contained. For example, the in-vivo device may be or may include a capsule or other unit where all the components are substantially contained within a container, housing or shell, and where the in-vivo device does not require any wires or cables to, for example, receive power or transmit information. The in-vivo device may communicate with an external receiving and display system to provide display of data, control, or other functions. For example, power may be provided by an internal battery or an internal power source, or using a wired or wireless power-receiving system. Other embodiments may have other configurations and capabilities. For example, components may be distributed over multiple sites or units; and control information or other information may be received from an external source.

Although embodiments of the invention are not limited in this regard, the term "contractile activity" as used herein may relate to or may include, for example, movement or contractions of a body lumen (e.g., the GI tract), closing and/or opening of a body lumen (e.g., rapid closing and/or opening of a body lumen), narrowing and/or widening of a body lumen (e.g., rapid narrowing and/or widening of a body lumen), existence or presence of contractions at a certain time and/or location, intestinal motility, intestinal contractions, or the like.

Figure 1:
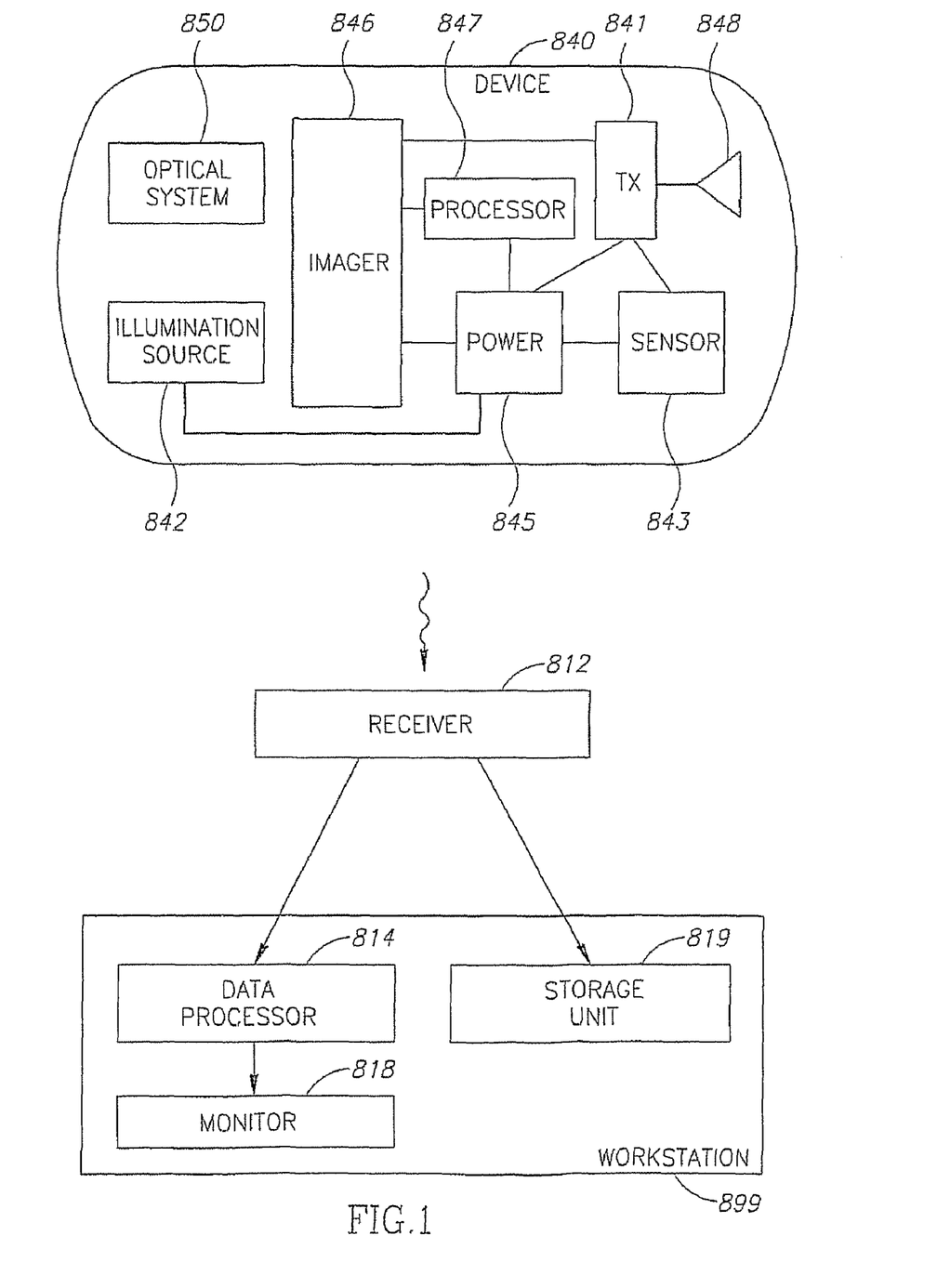
FIG. 1 is a schematic block diagram of an in-vivo sensing system in accordance with some embodiments of the invention.

FIG. 1 schematically illustrates an in-vivo sensing system in accordance with an embodiment of the present invention. In some embodiments, the system may include, for example, an in-vivo device 840 having an imager 846, an illumination source 842, a power source 845, and a transmitter 841. In some embodiments, device 840 may be implemented using a swallowable capsule, but other sorts of devices or suitable implementations may be used. Outside a patient's body may be, for example, an image receiver 812 (including or operatively connected to, for example, an antenna, an antenna belt, or an antenna array), a storage unit 819, a data processor 814, and a monitor 818. In one embodiment, for example, the storage unit 819, the data processor 814, and/or the monitor 818 may optionally be implemented as a workstation 899 which may include, for example, a multi-purpose or dedicated computer or computing platform.

Transmitter 841 may operate wirelessly, for example, by using radio waves; but in some embodiments, such as those where device 840 is or is included within an endoscope, transmitter 841 may transmit data via, for example, wire, optical fiber and/or other suitable methods.

Device 840 typically may be or may include an autonomous swallowable capsule, but device 840 may have other shapes and need not be swallowable or autonomous. Embodiments of device 840 are typically autonomous, and are typically self-contained. For example, device 840 may be a capsule or other unit where all the components are substantially contained within a container or shell, and where device 840 does not require any wires or cables to, for example, receive power or transmit information.

In some embodiments, device 840 may communicate with an external receiving and display system (e.g., through receiver 812) to provide display of data, control, or other functions. For example, power may be provided to device 840 using an internal battery, an internal power source, or a wireless system to receive power. Other embodiments may have other configurations and capabilities. For example, components may be distributed over multiple sites or units, and control information may be received from an external source.

In one embodiment, device 840 may include an in-vivo video camera, for example, imager 846, which may capture and transmit images of, for example, the GI tract while device 840 passes through the GI lumen. Other lumens and/or body cavities may be imaged and/or sensed by device 840. In some embodiments, imager 846 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In one embodiment, imager 846 in device 840 may be operationally connected to transmitter 841. Transmitter 841 may transmit images to, for example, image receiver 812, which may send the data to data processor 814 and/or to storage unit 819. Transmitter 841 may also include control capability, although control capability may be included in a separate component. Transmitter 841 may include any suitable transmitter able to transmit image data, other sensed data, and/or other data (e.g., control data) to a receiving device. For example, transmitter 841 may include an ultra low power Radio Frequency (RF) high bandwidth transmitter, possibly provided in Chip Scale Package (CSP). Transmitter 841 may transmit via antenna 848. Transmitter 841 and/or another unit in device 840, e.g., a controller or processor 847, may include control capability, for example, one or more control modules, processing module, circuitry and/or functionality for controlling device 840, for controlling the operational mode or settings of device 840, and/or for performing control operations or processing operations within device 840.

Power source 845 may include one or more batteries or power cells. For example, power source 845 may include silver oxide batteries, lithium batteries, other suitable electrochemical cells having a high energy density, or the like. Other suitable power sources may be used. For example, power source 845 may receive power or energy from an external power source (e.g., a power transmitter), which may be used to transmit power or energy to device 840.

In some embodiments, power source 845 may be internal to device 840, and/or may not require coupling to an external power source, e.g., to receive power. Power source 845 may provide power to one or more components of device 840, for example, continuously, substantially continuously, or in a non-discrete manner or timing, or in a periodic manner, an intermittent manner, or an otherwise non-continuous manner. In some embodiments, power source 845 may provide power to one or more components of device 840, for example, not necessarily upon-demand, or not necessarily upon a triggering event or an external activation or external excitement.

Optionally, in one embodiment, transmitter 841 may include a processing unit or processor or controller, for example, to process signals and/or data generated by imager 846. In another embodiment, the processing unit may be implemented using a separate component within device 840, e.g., controller or processor 847, or may be implemented as an integral part of imager 846, transmitter 841, or another component, or may not be needed. The optional processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In one embodiment, for example, the processing unit or controller may be embedded in or integrated with transmitter 841, and may be implemented, for example, using an ASIC.

In some embodiments, imager 846 may acquire in-vivo images, for example, continuously, substantially continuously, or in a non-discrete manner, for example, not necessarily upon-demand, or not necessarily upon a triggering event or an external activation or external excitement; or in a periodic manner, all intermittent manner, or an otherwise non-continuous manner.

In some embodiments, transmitter 841 may transmit image data continuously, or substantially continuously, for example, not necessarily upon-demand, or not necessarily upon a triggering event or an external activation or external excitement; or in a periodic manner, an intermittent manner, or an otherwise non-continuous manner.

In some embodiments, device 840 may include one or more illumination sources 842, for example one or more Light Emitting Diodes (LEDs), "white LEDs", Organic LEDs (OLEDs), or other suitable light sources. Illumination sources 842 may, for example, illuminate a body lumen or cavity being imaged and/or sensed. An optional optical system 850, including, for example, one or more optical elements, such as one or more lenses or composite lens assemblies, one or more suitable optical filters, or any other suitable optical elements, may optionally be included in device 840 and may aid in focusing reflected light onto imager 846 and/or performing other light processing operations.

Data processor 814 may analyze the data received via receiver 812 from device 840, and may be in communication with storage unit 819, e.g., transferring frame data to and from storage unit 819. Data processor 814 may also provide the analyzed data to monitor 818, where a user (e.g., a physician) may view or otherwise use the data, including, for example, image data, sensing data, location data, motility data, or other information. In one embodiment, data processor 814 may be configured for real time processing and/or for post processing to be performed and/or viewed at a later time. In the case that control capability (e.g., delay, timing, etc) is external to device 840, a suitable external device (such as, for example, data processor 814 or image receiver 812) may transmit one or more control signals to device 840. Monitor 818 may include, for example, one or more screens, monitors, or suitable display units. Monitor 818, for example, may display one or more images or a stream of images captured and/or transmitted by device 840, e.g., images of the GI tract or of other imaged body lumen or cavity. Additionally or alternatively, monitor 818 may display, for example, control data, location or position data (e.g., data describing or indicating the location or the relative location of device 840), orientation data, motility information, and/or other suitable data. In one embodiment, for example, both an image and its position or location may be presented using monitor 818 and/or may be stored using storage unit 819. Other systems and methods of storing and/or displaying collected image data and/or other data may be used.

In some embodiments, in addition to or instead of revealing pathological or other conditions of the GI tract or other body lumens, the system may provide information about the location of these conditions. Suitable tracking devices and methods are described herein, as well as in embodiments of the above-mentioned U.S. Pat. No. 5,604,531 and/or U.S. patent application Ser. No. 10/150,018, titled "Array System and Method for Locating an In-Vivo Signal Source", filed on May 20, 2002, published on Nov. 21, 2002 as United States Patent Application Publication Number 2002/0173718, both of which assigned to the common assignee of the present invention and fully incorporated herein by reference. Other suitable location identification systems and methods may be used in accordance with embodiments of the present invention.

Typically, device 840 may transmit image information in discrete portions. Each portion may typically correspond to an image or a frame; other suitable transmission methods may be used. For example, in some embodiments, device 840 may capture and/or acquire an image once every half second, and may transmit the image data to receiver 812. Other constant and/or variable capture rates and/or transmission rates may be used.

Typically, the image data recorded and transmitted may include digital color image data; in alternate embodiments, other image formats (e.g., black and white image data) may be used. In some embodiments, each frame of image data may include 256 rows, each row may include 256 pixels, and each pixel may include data for color and brightness according to known methods. According to other embodiments, a 320 by 320 pixel imager may be used; other imagers having other suitable pixel sizes may be used. Pixel size may be, for example, between 5 to 6 microns; other suitable sizes may be used. According to some embodiments, pixels may be each fitted with a micro lens. For example, a Bayer color filter may be applied. Other suitable data formats may be used, and other suitable numbers or types of rows, columns, arrays, pixels, sub-pixels, boxes, super-pixels and/or colors may be used.

Optionally, device 840 may include one or more sensors 843, instead of or in addition to a sensor such as imager 846. Sensor 843 may, for example, sense, detect, determine and/or measure one or more values of properties or characteristics of the surrounding of device 840. For example, sensor 843 may include a pH sensor, a temperature sensor, an electrical conductivity sensor, a pressure sensor, or any other known suitable in-vivo sensor.

In some embodiments, device 840 may be capable of one way or two-way communication. For example, device 840 may be able to transmit data (e.g., sensed data, image data, localization data, or the like) using transmitter 841 to external receiver/recorder 812. Optionally, device 840 may be able to receive data (e.g., control data, instructions, commands, parameter values, modification of setting or parameters, activation instructions, deactivation instructions, or the like) from an external transmitter or transceiver. For example, in one embodiment, device 840 may optionally include a receiver able to receive signals (e.g., transmitter 841 may optionally be implemented as a transceiver or transmitter-receiver); and receiver/recorder 812 may optionally be implemented as a transceiver or transmitter-receiver able to transmit signals to device 840. Other suitable one-way or two-way communication mechanisms may be used.

In accordance with some embodiments of the invention, localization data may be determined using, for example, data collected by or transmitted by an in-vivo device (e.g., device 840 or another signal source) separate from location data itself. For example, localization data may be inherent in a signal sent by the in-vivo device 840, or may be in a beacon sent by the in-vivo device 840, while other and additional data such as sensing data (e.g., image data, pH data, etc.) may be sent separately from localization data. In one embodiment, sensing data may be considered non-localization data collected by the in-vivo device 840. In some embodiments, localization data may be inherent in a data signal which primarily contains sensed data.

In some embodiments, image data and other collected data may be stored for short-term or long term periods, transferred to other locations or devices, processed and/or analyzed. A health professional may use the images to diagnose pathological conditions of the GI tract or other body parts, and, the system may provide information about the location of these pathologies. In one embodiment, the data processor storage unit 819 may first collect data and then may transfer the data to the data processor 814, such that the image data is not viewed in real time. In an alternate embodiment, other configurations may allow real time viewing, and motility data and/or contractile activity data may be calculated and displayed substantially in real time.

The monitor 818 may present image data, preferably in the form of still and/or moving pictures, and in addition may present other information. For example, in one embodiment, the monitor may present the absolute time elapsed for the current image being shown, relative or absolute information about contractile activity over the course of device 840 through the GI tract, contractile activity data or indicators, and/or the time corresponding to the current image or other data being displayed. Absolute time elapsed for the current image being shown may be, for example, the amount of time that elapsed between the moment the device 840 was first activated and the image receiver 812 started receiving transmissions from the device 840, and the moment that the current image being displayed was captured. Various methods may be used to display contractile activity information, e.g., as discussed herein. In some embodiments, various types of information may be displayed in windows or other screen portions, and/or multiple monitors may be used to display image data, motility data, contractile activity data, localization data, and/or other data.

While in some embodiments, information gathering, storage and processing may be performed by certain units, the system and method of the present invention may be practiced with alternate configurations. For example, components allowing contractile activity measurement and/or analysis may be located inside device 840 (e.g., a swallowable capsule) or, alternatively, on a portable device (e.g., receiver 812) which may be worn on the patient. Furthermore, the components gathering image information need not be contained in a capsule, but may be contained in any other vehicle suitable for traversing a lumen in a human body, such as an endoscope, a stent, a catheter, a needle, or other suitable devices.

In some embodiments, multiple in-vivo images may be analyzed in order to produce information about contractile activity, e.g., contractile activity of the GI tract. The information produced may include, for example, an indication of contractile activity, an indication of absence of contractile activity, an indication of a contraction, an indication of multiple contractions, an indication of an absence of contraction, information about the time and/or location of contraction(s), information about frequency and/or number of contractions, information about strength (e.g., relative strength or absolute strength) and/or duration (e.g., time length) of contraction(s), an indication that contractile activity is normal or abnormal, or other suitable information.

In some embodiments, analysis of one or more properties of a set of multiple in-vivo images (e.g., of a set or a sequence of in-vivo images) may be used in order to determine information about contractile activity. For example, an analysis of multiple, e.g., consecutive, in-vivo images may be used to detect and/or measure a contraction or multiple contractions.

In some embodiments, the detection of a contraction may be performed based on a property, or multiple properties, which may be measured across multiple images. For example, the value of a measured property may be different across multiple images, such that a contraction may be indicated. In some embodiments, for example, a contraction (or an absence thereof) may be determined based on comparison of a value of a property across multiple (e.g., consecutive) images.

In some embodiments, for example, an intensity level of an image (or an image portion) may be measured or calculated, and modification of the intensity level across multiple images may be used to determine a contraction associated with one or more of the images. For example, a series of K in-vivo images may be analyzed, for example, a set of 9 consecutive in-vivo images.

In some embodiments, for example, in absence of contractions, the in-vivo imaging device 840 may travel through the body lumen and may acquire in-vivo images. For example, in absence of contractions, or during a relatively low contractile activity, an outer portion (e.g., a ring-shaped portion) of the acquired in-vivo images may be relatively bright, e.g., due to reflection of light from body lumen walls; whereas an inner portion (e.g., a substantially central portion) of the in-vivo images may be relatively dark, e.g., since the in-vivo images may include a portion corresponding to the body lumen through which the device 840 travels. In contrast, a contraction may cause the body lumen to contract, such that the lumen walls may "close" and/or narrow on the in-vivo device 840. As a result, in-vivo images acquired during a contraction may be relatively bright, or may include a relatively larger bright portion. Additionally or alternatively, in-vivo images acquired during a contraction may not include a dark portion, or may include only a relatively small dark portion. In some embodiments, for example, a contraction may include a cycle of rapid closing and/or rapid opening of a body lumen (e.g., the GI tract or a portion thereof), thereby causing a variation (e.g., a sharp variation) in one or more properties of in-vivo images acquired by the in-vivo device 840 (e.g., brightness level, darkness level, image intensity, grey-level intensity, or the like). For example, in some embodiments, the brightness level or the global intensity of in-vivo images acquired during a contraction may be relatively higher than the brightness level or the global intensity of in-vivo images acquired at times and/or locations in which a contraction does not take place. In some embodiments, for example, when the body lumen is "closed" or contracts, the light illuminated by in-vivo device 840 may be reflected by the intestinal walls; whereas when the body lumen is "open" or does not contract, the light illuminated by in-vivo device 840 may be dissipated along the intestinal tube. Therefore, measurement and/or analysis of a parameter corresponding to global image illumination (e.g., brightness, darkness, image intensity, or the like) may be used as indicator of the presence or the absence of contraction(s) and/or contractile activity.

Figure 2:
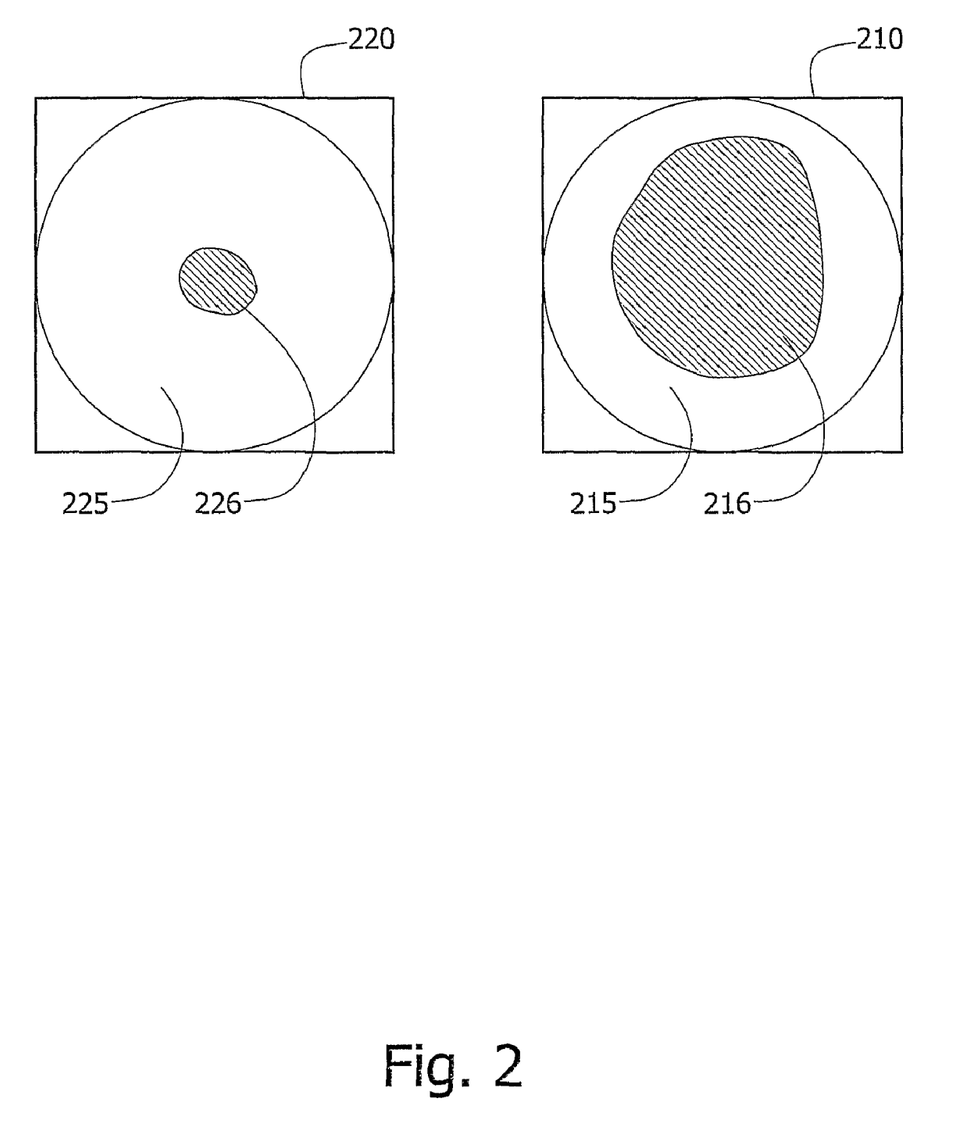
FIG. 2 is a schematic illustration of two demonstrative in-vivo images in accordance with some embodiments of the invention.

Reference is made to FIG. 2, which schematically illustrates two demonstrative in-vivo images 210 and 220 in accordance with some embodiments of the invention. In-vivo image 210 may demonstrate an in-vivo image acquired (e.g., by device 840 of FIG. 1) in absence of contractions, or when contractile activity is relatively low. A relatively dark portion 216 may correspond to the body lumen through which the in-vivo device 840 travels; whereas a relatively brighter portion 215 may correspond to the walls of the body lumen, e.g., since the walls of the body lumen may reflect light illuminated by device 840.

In contrast, in-vivo image 220 may demonstrate an in-vivo image acquired (e.g., by device 840 of FIG. 1) during a contraction, or when contractile activity is relatively high. A relatively dark portion 226 may correspond to the body lumen through which the in-vivo device 840 travels; whereas a relatively brighter portion 225 may correspond to the walls of the body lumen, e.g., since the walls of the body lumen may reflect light illuminated by device 840.

As shown in FIG. 2, the bright portion 225 of image 220 (acquired during a contraction) may be larger than the bright portion 215 of image 210 (acquired in absence of contractions). Additionally or alternatively, the dark portion 226 of image 220 (acquired during a contraction) may be smaller than the dark portion 216 of image 210 (acquired in absence of contractions). In some embodiments, optionally, image 220 (acquired during a contraction) may not include dark portion 226 at all, or may include a dark portion 226 which may be significantly small.

In some embodiments, a global brightness level of image 220 may be greater than a global brightness level of image 210. In some embodiments, a global intensity parameter corresponding to image 220 may indicate that image 220 is brighter, or significantly brighter, relative to image 210.

Figure 3:
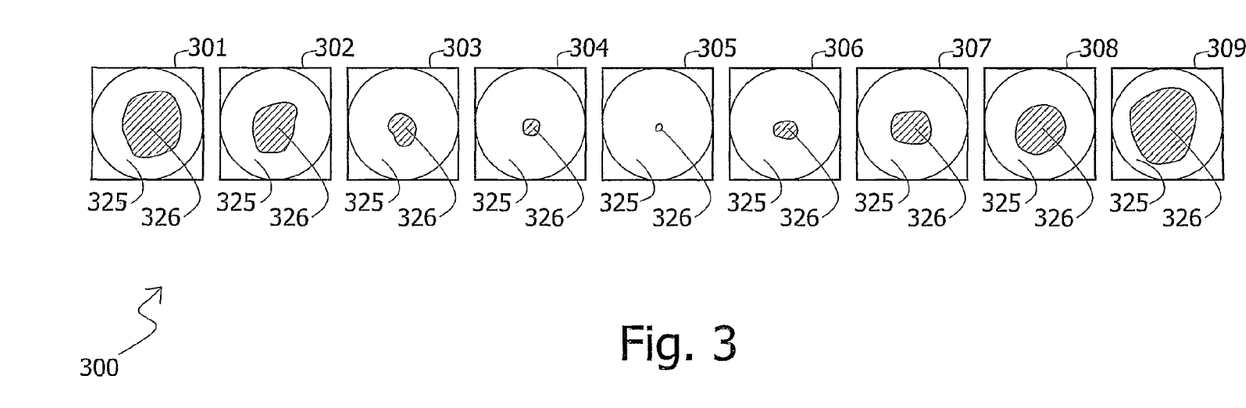
FIG. 3 is a schematic illustration of a set of demonstrative in-vivo images in accordance with some embodiments of the invention.

Reference is made to FIG. 3, which schematically illustrates a set 300 of demonstrative in-vivo images in accordance with some embodiments of the invention. For example, in some embodiments, set 300 may include nine in-vivo images 301-309; other suitable number of in-vivo images may be used to determine contractions and/or contractile activity information. In FIG. 3, the dark (or relatively darker) portions of images 301-309 are indicated with numeral 326, whereas the bright (or relatively brighter) portions of images 301-309 are indicated with numeral 325.

As shown in FIG. 3, the dark portion 326 may have a relatively large size in image 301; for example, dark portion 326 may occupy approximately forty percent of the area of image 301. The size of dark portion 326 may gradually decrease across images 301 to 305, and may be smallest in image 305. Optionally, in some embodiments, dark portion 326 of image 305 may be significantly small, e.g., approximately one percent of the area of image 305, or may not be included at all in image 305. Then, the size of dark portion 326 may gradually increase across imaged 305 to 309, and may be of a relatively large size in image 309.

The set 300 of in-vivo images 301-309 may correspond to an in-vivo contraction, or to a cycle of contractile activity. For example, image 305 may include the largest bright portion 325, and/or the smallest dark portion 326, and/or may be associated with the highest value of global image brightness or global image intensity. Image 305 may thus correspond to a peak of a contraction or to a peak of contractile activity. In one embodiment, image 301 and/or image 309 may correspond to a time and/or a location of absence of contractile activity; in another embodiment, image 301 may correspond to a time and/or a location of a beginning of a contraction, whereas image 309 may correspond to a time and/or a location of an ending of a contraction.

In some embodiments, for example, a series of K in-vivo images may be identified, such that a first portion of the K images may be relatively darker (e.g., may have a relatively smaller value of brightness or global intensity); a second portion of the K images may be relatively brighter (e.g., may have a relatively higher value of brightness or global intensity); and a third portion of the K images may be relatively darker (e.g., may have a relatively higher value of brightness or global intensity). In some embodiments, for example, a first group of in-vivo images and a second group of in-vivo images may be darker (e.g., may have a lower value of global intensity or brightness); whereas a third group of in-vivo images, which may be acquired after the first group and before the second group, may be brighter (e.g., may have a higher value of global intensity or brightness), thereby indicating a contraction or a peak of a contraction corresponding to the in-vivo images of the third (e.g., middle) group. Other suitable patterns may be identified and/or used in accordance with embodiments of the invention.

Figure 4:
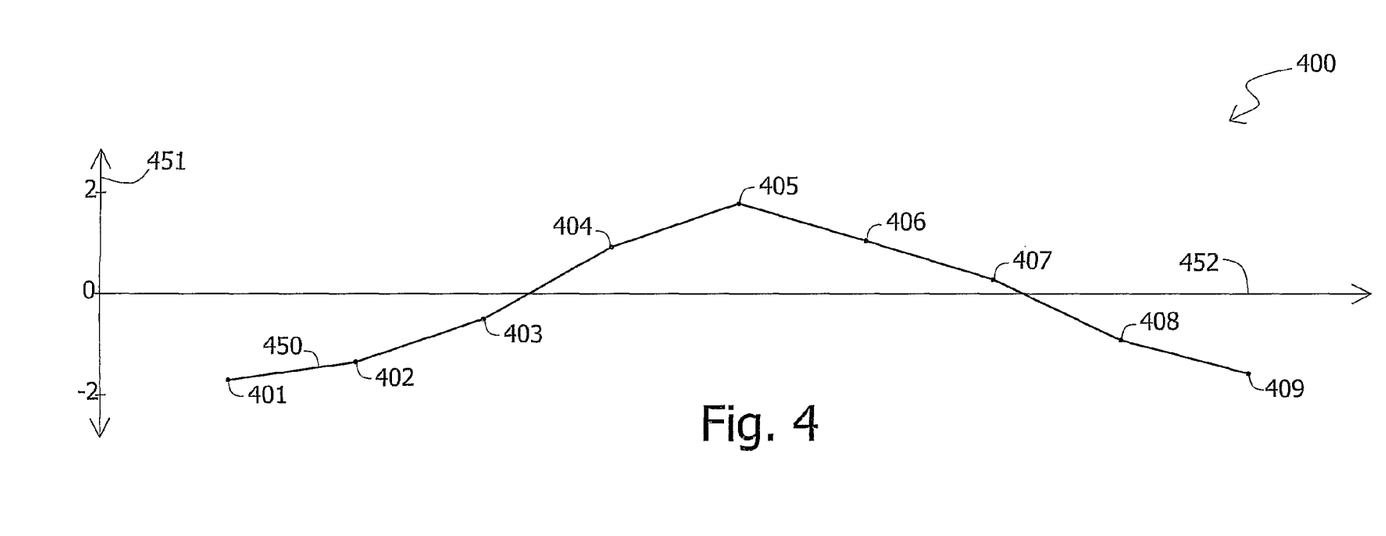
FIG. 4 is a schematic illustration of a graph of in-vivo image intensity in accordance with some embodiments of the invention.

Reference is made to FIG. 4, which schematically illustrates a graph 400 of in-vivo image intensity in accordance with some embodiments of the invention. A vertical axis 451 may indicate, for example, an intensity level (e.g., a global intensity level), or a brightness level of an in-vivo image or of a portion of an in-vivo image. Vertical axis 451 may indicate or correspond to other parameters, for example, relative or absolute brightness, relative or absolute darkness, relative or absolute image intensity, relative or absolute grey-level or grey-scale intensity, hue, saturation, color, color attributes, channels, color channels, color components (e.g., red component, green component, blue component, etc.), contrast, or the like. A horizontal axis 452 may indicate, for example, a sequential or a consecutive number of in-vivo images, a set or series of consecutive or non-consecutive in-vivo images. Horizontal axis 451 may indicate or correspond to other parameters, for example, time that elapses while the in-vivo device travels in-vivo, in-vivo location of the in-vivo device, or the like.

A set of points 401-409 in graph 400 may correspond, for example, to the set of images 301-309 of FIG. 3, respectively. For example, point 401 may correspond to in-vivo image 301, point 402 may correspond to in-vivo image 302, etc. A line 450 may connect some or all of the points 401-409.

In some embodiments, points 401-409 and/or line 450 may indicate the presence of a contraction or other contractile activity corresponding to some or all of in-vivo images 301-309. For example, in some embodiments, line 450 may correspond to a contraction, point 405 may correspond to a peak of a contraction, point 401 or point 402 may correspond to a beginning of a contraction, point 408 or point 409 may correspond to an ending of a contraction, or the like.

In some embodiments, the pattern, shape, angle(s), slant, curvature, outline and/or other properties of line 450 (and/or of one or more of points 401-409) may be determined or analyzed. The analysis may be performed, for example, ex-vivo by data processor 814 of workstation 899 of FIG. 1, and/or in-vivo by processor 847 of FIG. 1. Based on the analysis, workstation 899 and/or monitor 818 may display or otherwise present (e.g., using an audible or a visual indication) information related to contraction(s) and/or contractile activity. For example, in some embodiments, in-vivo images corresponding to a contraction, to a peak of a contraction, to a beginning of a contraction, to an ending of a contraction, or the like, may be tagged, marked, highlighted or otherwise indicated.

Although some portions of the discussion herein may relate, for demonstrative purposes, to analysis of contraction(s) and/or contractile activity based on (or corresponding to) nine in-vivo images, other suitable numbers of in-vivo images may be used, and some or all of the analyzed in-vivo imaged need not be consecutive. In some embodiments, for example, a contraction may be determined to correspond to a series of nine consecutive in-vivo images, e.g., acquired at a frame capture rate of approximately two in-vivo images per second. In some embodiments, for example, a contraction may be determined to correspond to a series of consecutive in-vivo images acquired in-vivo within a time period of approximately four seconds or five seconds. Other suitable numbers, time periods or frame capture rates may be used.

In some embodiments, for example, properties other than global brightness, darkness or image intensity may be used to determine contraction(s) and/or contractile activity. For example, in some embodiments, the size or the area of a dark portion (or a bright portion) of in-vivo images may be analyzed; the height and/or width of a dark portion (or a bright portion) of in-vivo images may be analyzed; the position or location (e.g., within the in-vivo image) of a dark portion (or a bright portion) of in-vivo images may be analyzed; or other suitable properties may be analyzed.

In some embodiments, the intensity variation across a series of in-vivo images may be measured in relation to a locally normalized mean intensity level. For example, in some embodiments, the following equation may be used:

$$In = I - Iaverage \qquad \text{Equation 1}$$

wherein I represents a mean grey-level intensity of an in-vivo image; In represents a locally normalized mean intensity level; and Iaverage represents an average intensity calculated for a series of in-vivo images, e.g., for a set of nine consecutive in-vivo images. For example, Iaverage may be calculated by adding together the intensity value of K in-vivo images, and dividing the result by K. Other suitable equations or calculations may be used.

In some embodiments, for example, a series of in-vivo images may be analyzed in order to identify in-vivo images which may correspond to a contraction or to certain contractile activity. For example, in some embodiments, hundreds or thousands of in-vivo images may be analyzed, e.g., by calculating a value of In for some or all of the in-vivo images in the series. Subsets of sequential or consecutive in-vivo images having a positive In value may be extracted from the series of analyzed images. The in-vivo image corresponding to the highest value of In in a subset of in-vivo images may be identified as a central image for a contraction possibly corresponding to that subset of in-vivo images.

In some embodiments, for example, the normalized intensity In may be calculated for an in-vivo image, e.g., for substantially each in-vivo image. The calculation may be performed, for example, based on the sum of intensity values of the pixels (or other image portions) of the in-vivo image, and by taking into account image intensity value(s) of one or more (e.g., four) prior images and image intensity value(s) of one or more (e.g., four) subsequent images.

In some embodiments, for example, the normalized intensity In of the n-th in-vivo image may be calculated as follows: the image intensity value of the n-th in-vivo image, may be added together with the image intensities of the four in-vivo images that precede the n-th in-vivo image and with the image intensities of the four in-vivo images that follow the n-th in-vivo image, and the sum may be divided by nine. The result may represent the normalized intensity if the n-th in-vivo image, calculated based on a set of nine in-vivo images in which the n-th image is the central image.

In some embodiments, a relatively brighter in-vivo image (e.g., due to a contraction) may correspond to a positive value of image intensity In; whereas a relatively darker in-vivo image (e.g., due to absence of contractions) may correspond to a negative value of image intensity In. In some embodiments, for example, an in-vivo image having an image intensity value higher than the image intensity values of its neighboring images (e.g., one or more previous images and one or more following images), may indicate that the in-vivo image corresponds to an intestinal contraction or to a peak of intestinal contraction.

In some embodiments, the normalized image intensity parameter In may have a relatively high value when the analyzed in-vivo image corresponds to an intestinal contraction; whereas the normalized image intensity parameter In may have a relatively low value, or a pseudo-random value, at a non-contraction time and/or non-contraction locations.

In some embodiments, a filter or a pre-filter mechanism may be used (e.g., by data processor 814 of workstation 899) in order to filter-in or otherwise select in-vivo images having a positive value of normalized image intensity, or to filter-out or otherwise deselect in-vivo images having a negative value (or a zero value) of normalized image intensity. In some embodiments, in-vivo images having a normalized image intensity which is greater than a threshold value may be filtered-in or selected; whereas in-vivo images having a normalized image intensity which is lower than (or equal to) a threshold value may be, filtered-out or deselected. In one embodiment, for example, a discriminant function may be associated with an in-vivo image such that, for example, the discriminant function may have a first value (e.g., "1") if the normalized image intensity is greater than the threshold value; whereas the discriminant function may have a second value (e.g., "−1") if the normalized image intensity is smaller than or equal to the threshold value. The threshold value may be implemented, for example, using a constant or modifiable parameter (e.g., a tuning parameter), or may be pre-set or dynamically set to certain values in accordance with specific implementations.

In some embodiments, for example, in-vivo images associated with the second value of discriminant function may be rejected, deselected, filtered-out or discarded; whereas in-vivo images associated with the first value of discriminant function may be selected, marked, tagged, kept or filtered-in. In some embodiments, the selected or filtered-in images may be used to generate output indicating contractile activity information, or may be used as input to other stages or phases of analysis or filtering to further generate contractile activity information.

Figure 5:
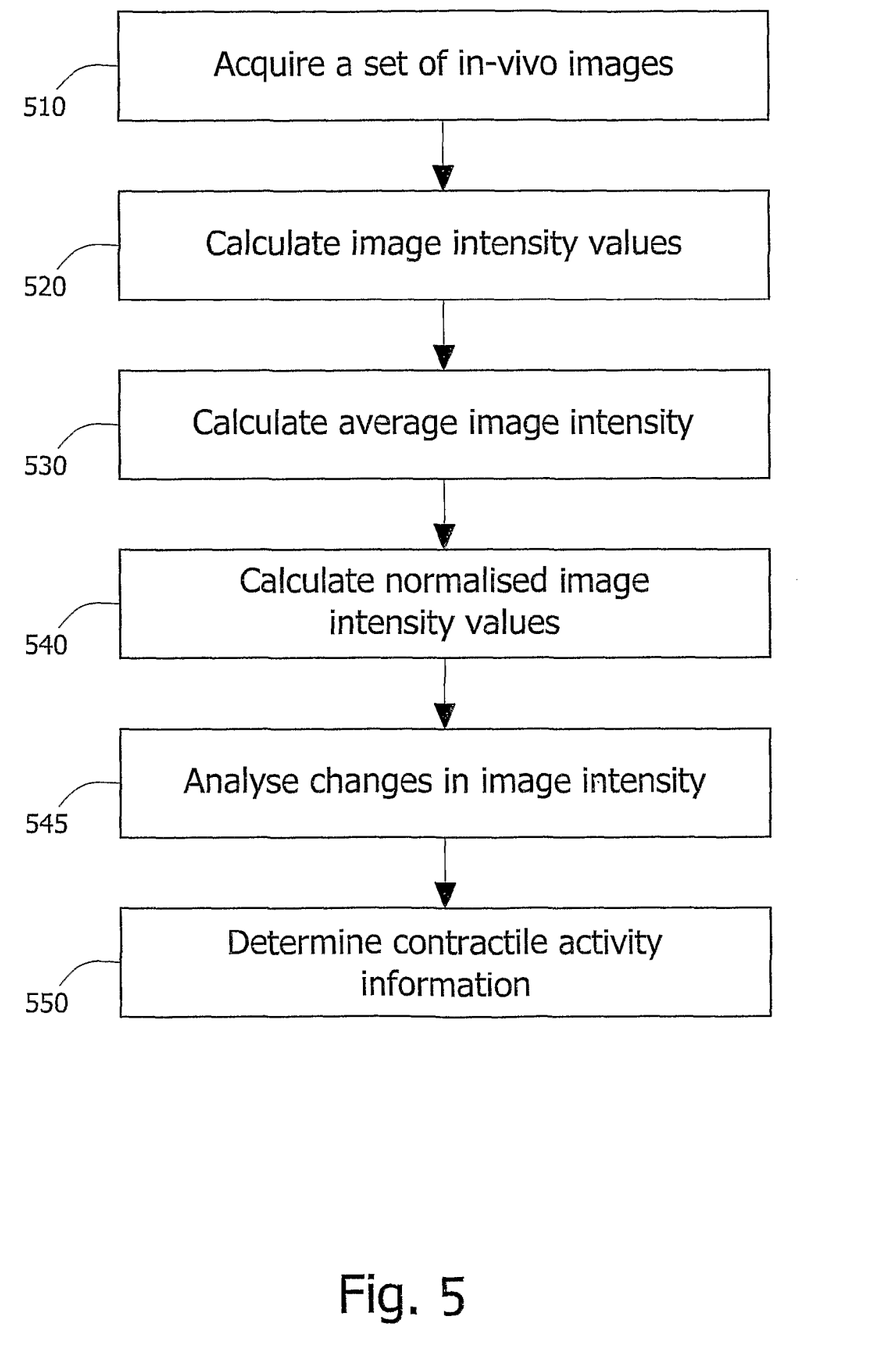
FIG. 5 is a flow-chart of a method of measurement and analysis of contractile activity in accordance with some embodiments of the invention.

Reference is made to FIG. 5, which is a flow-chart of a method of measurement and analysis of contractile activity in accordance with some embodiments of the invention. The method may be used, for example, in conjunction with the system of FIG. 1, with in-vivo imaging device 840 of FIG. 1, and/or with other suitable devices and systems.

In some embodiments, as indicated at box 510, the method may optionally include, for example, acquiring a set of in-vivo images. For example, a set of nine consecutive in-vivo images may be acquired, e.g., at a frame capture rate of approximately two images per second, by in-vivo imaging device 840 of FIG. 1.

In some embodiments, as indicated at box 520, the method may optionally include, for example, calculating an image intensity value for each of the nine in-vivo images.

In some embodiments, as indicated at box 530, the method may optionally include, for example, calculating an average image intensity value corresponding to the nine in-vivo images. For example, the nine image intensity values calculated in the operation of box 520, may be added together, and the sum may be divided by nine.

In some embodiments, as indicated at box 540, the method may optionally include, for example, calculating a normalized image intensity value corresponding to each of the nine in-vivo images. For example, the normalized image intensity value of a certain in-vivo image may be calculated by subtracting the average image intensity value (calculated at box 530) from the image intensity value of that image (calculated at box 520).

In some embodiments, as indicated at box 545, the method may optionally include, for example, analyzing change(s), variation(s) and/or or modification(s) of in-vivo image intensity values, e.g., of normalized image intensity values corresponding to multiple in-vivo images and/or to in-vivo images acquired within a pre-defined time period. The analysis may be performed, for example, in relation to a set of in-vivo images, in relation to multiple (e.g., consecutive or non-consecutive) in-vivo images, over a pre-defined time period in which in-vivo images may be acquired, or the like. In one embodiment, for example, the analysis may be performed in relation to nine consecutive in-vivo images (or other numbers of consecutive or non-consecutive in-vivo images), in relation to multiple in-vivo images acquired within approximately four or five seconds (or other time periods), or the like.

In some embodiments, as indicated at box 550, the method may optionally include, for example, determining contractile activity information (e.g., a contraction, or an absence thereof) corresponding to one or more in-vivo images based on the calculated normalized image intensity values. In one embodiment, for example, an in-vivo image having a relatively high value, or substantially the highest value, of normalized image intensity, may be determined to correspond with a contraction or with a peak of a contraction. In another embodiment, for example, a non-random pattern may be identified for one or more normalized image intensity values, e.g., a gradual increase followed by a gradual increase, thereby indicating a contraction or a peak of a contraction. Other determinations may be performed, and the determination result may be indicated or otherwise presented or displayed.

Other operations or sets of operations may be used in accordance with embodiments of the invention. In some embodiments, operations may be performed, for example, in real-time, substantially in real-time, while the in-vivo device is in-vivo, while the in-vivo device acquires images and/or transmits data, ex-vivo, or the like.

In some embodiments, for example, contraction(s) and/or contractile activity information may be detected, determined and/or measured based on an analysis of multiple (consecutive or non-consecutive) in-vivo images, based on an analysis of an image stream, based on an analysis of an image stream over a pre-defined time period, or the like. In some embodiments, for example, detection, determination and/or measurement of contraction(s) and/or contractile activity may be based on an analysis that takes into account multiple in-vivo images.

In some embodiments, detection, determination and/or measurement of contraction(s) and/or contractile activity may be implemented using a contractile activity detector and/or a contractions detector. The contractile activity detector and/or the contractions detector may be implemented, for example, as a stand-alone unit or module, as part of data processor 814, as part of workstation 899, as part of receiver/recorder 812, as part of processor 847, as a separate or integrated unit or device, or the like. In one embodiment, the contractions detector may be a sub-unit or a module of the contractile activity detector, or vice versa. For example, the sub-system described herein with reference to FIG. 6 may be a demonstrative example of an implementation of a method in accordance with some embodiments of the invention, may be a demonstrative example of a module or a unit of a contractions detector, may be a demonstrative example of a module or a unit of a contractile activity detector, or the like.

Figure 6:
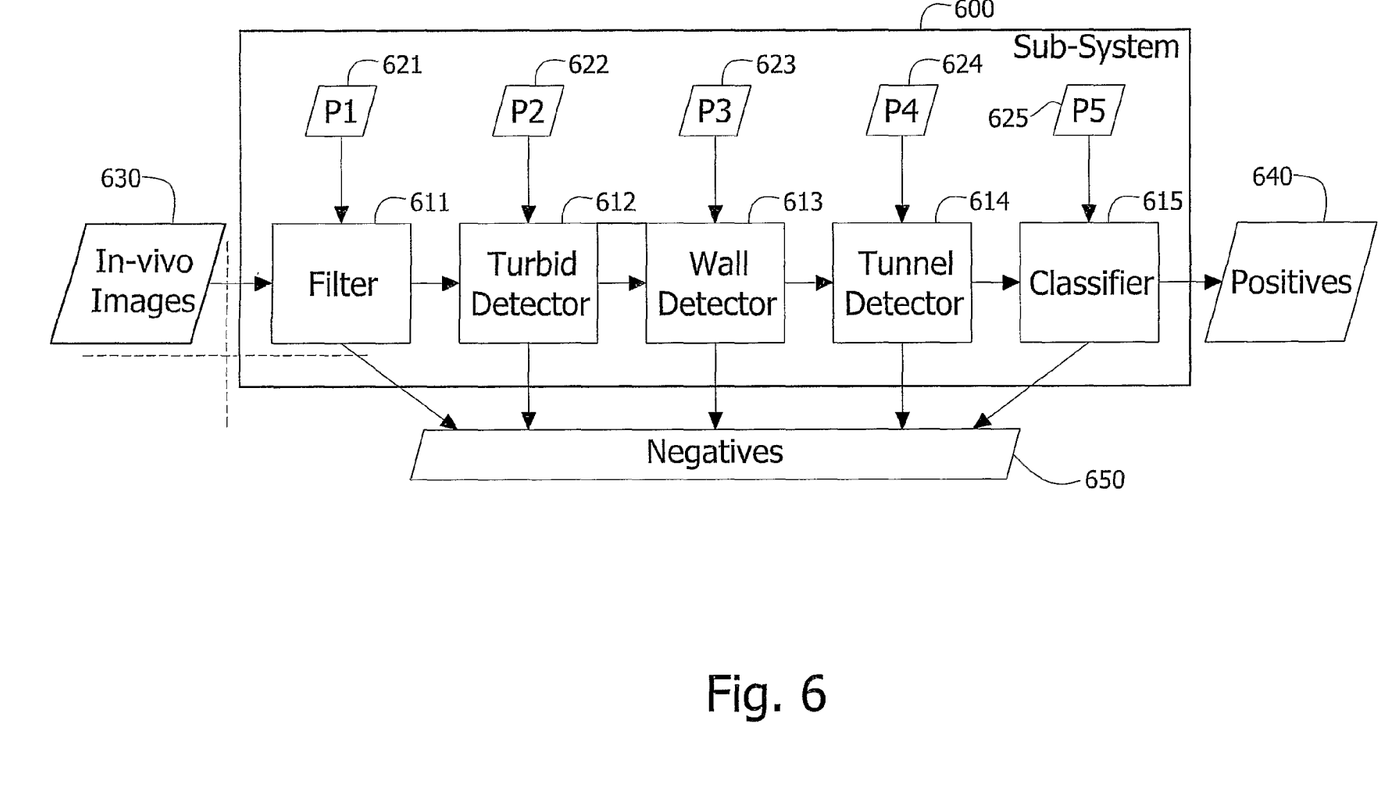
FIG. 6 is a schematic illustration of a sub-system for intestinal contractile activity assessment in accordance with some embodiments of the invention.

Reference is made to FIG. 6, which schematically illustrates a sub-system 600 for intestinal contractile activity assessment in accordance with some embodiments of the invention. Sub-system 600 may be implemented, for example, as part of data processor 814, as part of workstation 899, as part of receiver/recorder 812, as part of processor 847, as a separate or integrated unit or device, or the like.

Sub-system 600 may include, for example, a filter 611, a turbid detector 612, a wall detector 613, a tunnel detector 614, and a classifier 615. In some embodiments, sub-system 600 may include multiple stages or phases of contractile activity analysis. For example, filter 611 may be included in a first stage of contractile activity analysis; turbid detector 612, wall detector 613 and tunnel detector 614 may be included in a second stage of contractile activity analysis; and classifier 615 may be included in a third stage of contractile activity analysis. In some embodiments, for example, the output of the first stage may be used as input by the second stage, and the output of the second stage may be used as input by the third stage. Other number of stages may be used, and components may be distributed in various other ways among stages.

Sub-system 600 may receive an input 630, for example, multiple in-vivo images, e.g., a series of images acquired by in-vivo imaging device 840 of FIG. 1, a video sequence including multiple frames, or the like. In some embodiments, filter 611 may perform an analysis of the incoming in-vivo images based on brightness, darkness, and/or image intensity. In-vivo images which may correspond to contractions and/or to contractile activity of interest (which may be referred herein as "positives") may be passed by filter 611 to turbid detector 612; whereas in-vivo images which may not correspond to contractions and/or to contractile activity of interest (which may be referred herein as "negatives") may be passed by filter 611 to an output 650 of "negatives".

In some embodiments, turbid detector 612, wall detector 613 and tunnel detector 614 may filter-out (e.g., to output 650) in-vivo images which are determined to be "invalid", e.g., due to occlusion(s), or due to an inappropriate or non-optimal orientation of the in-vivo imaging device. The classifier 615 may perform a classification analysis, for example, using a Support Vector Machine (SVM) classification algorithm. The classifier 615 may perform a classification analysis, for example, using a Relevance Vector Machine (RVM) classification algorithm or a Laplacean RVM classification algorithm, which is a variation of the RVM using independent double-exponential (Laplace) parameters distributions. The accuracy of the results of the classifier 615 may be improved by performing feature selection and determining the most suitable subset of variables to consider during the classification process, for example by using methods known in the art such as the Boosted Lasso algorithm. The "positive" images may be transferred as output from classifier 615, for example, as output 640 of sub-system 600.

In some embodiments, output 640 may include substantially only in-vivo images that correspond to contractions. In other embodiments, output 640 may include substantially only in-vivo images that correspond to certain (e.g., pre-defined) contractile activity of interest. In yet other embodiments, output 640 may include in-vivo images that correspond to times and/or locations that are characterized by absence of contractions, e.g., in-vivo images that are determined to correspond to non-contractions. In still other embodiments, output 640 may include multiple streams of output, for example, a first stream including in-vivo images that correspond to contractions, and a second stream including in-vivo images that correspond to non-contractions. Other suitable outputs may be used.

In some embodiments, various operations may be performed in relation to the output 640. For example, the output 640 or portions thereof may be displayed or presented (e.g., using monitor 818 and/or workstation 899), may be stored (e.g., using storage unit 819), may be further processed or analyzed (e.g., using processor 847 and/or data processor 814), or the like.

In some embodiments, optionally, filter 611 may further receive as an input 621 one or more values denoted P1, which may be used by filter 611 as parameters or settings which may control, tune or modify the operation of filter 611, or may be used as parameters or threshold values in algorithms used by filter 611.

In some embodiments, optionally, turbid detector 612 may further receive as an input 622 one or more values denoted P2, which may be used by turbid detector 612 as parameters or settings which may control, tune or modify the operation of turbid detector 612, or may be used as parameters or threshold values in algorithms used by turbid detector 612.

In some embodiments, optionally, wall detector 613 may further receive as an input 623 one or more values denoted P3, which may be used by wall detector 613 as parameters or settings which may control, tune or modify the operation of wall detector 613, or may be used as parameters or threshold values in algorithms used by wall detector 613.

In some embodiments, optionally, tunnel detector 614 may further receive as an input 624 one or more values denoted P4, which may be used by tunnel detector 614 as parameters or settings which may control, tune or modify the operation of tunnel detector 614, or may be used as parameters or threshold values in algorithms used by tunnel detector 614.

In some embodiments, optionally, classifier 615 may further receive as an input 625 one or more values denoted P5, which may be used by classifier 615 as parameters or settings which may control, tune or modify the operation of classifier 615, or may be used as parameters or threshold values in algorithms used by classifier 615.

Figure 7:
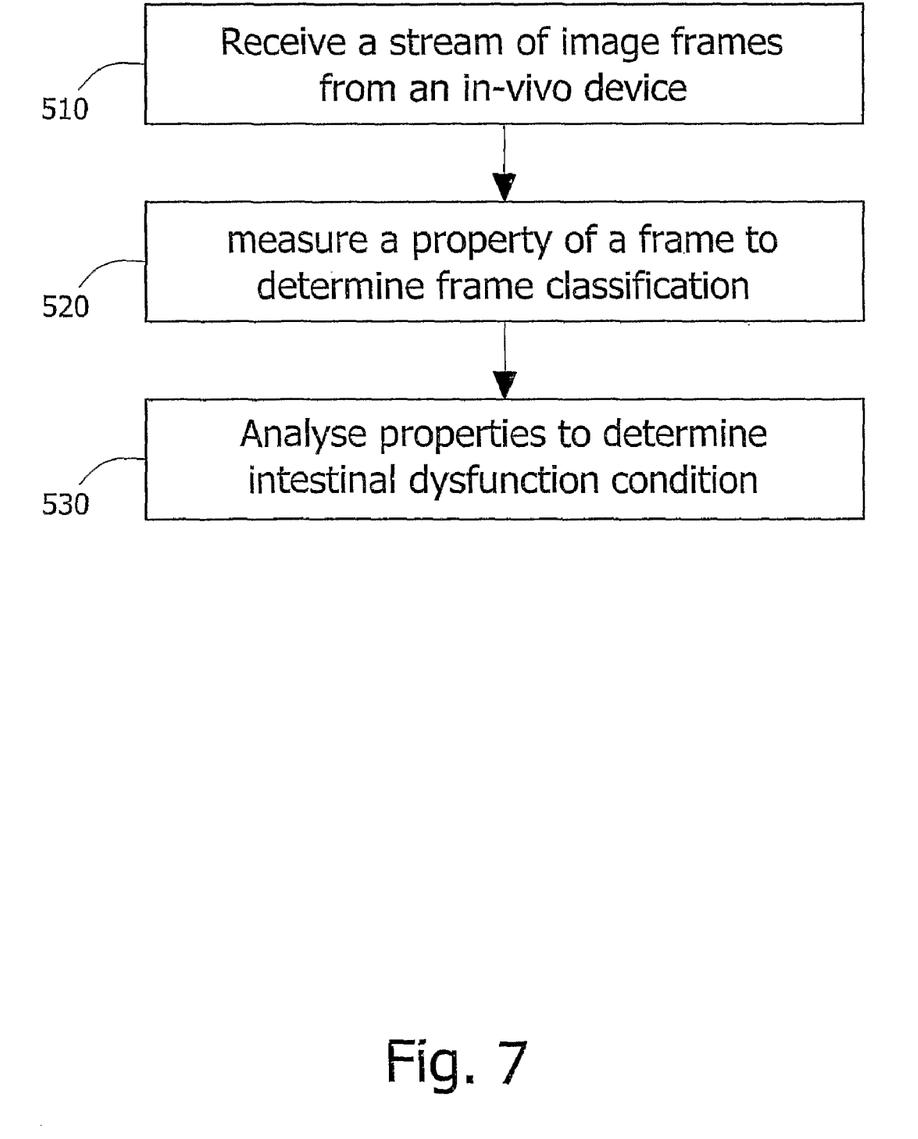
FIG. 7 is a flowchart of a method of determining intestinal dysfunction condition in accordance with some embodiments of the invention.

Reference is made to FIG. 7, which is a flow-chart of a method of determining intestinal dysfunction condition in accordance with some embodiments of the invention. The method may be used, for example, in conjunction with the system of FIG. 1, with in-vivo imaging device 840 of FIG. 1, and/or with other suitable devices and systems. The method may be used, for example, to automatically diagnose intestinal dysfunctions.

In some embodiments, as indicated at box 710, the method may optionally include, for example, receiving a stream of image frames from an in vivo device. For example, a video stream of consecutive in-vivo image frames may be received, e.g., at a frame capture rate of approximately two images per second, by in-vivo imaging device 840 of FIG. 1. The stream may include thousands of image frames.

In some embodiments, as indicated at box 720, the method may optionally include, for example, measuring a property of a frame to determine frame classification. Frame classification may include classifying each frame into one or more categories. For example, contractile activity frames may be a classification category, e.g., including frames that show occlusive contractions or frames that show non occlusive contractions. In some embodiments, static frames (e.g., sequences of frames that show no apparent motion or little apparent motion of the capsule), turbid frames (e.g., frames that show intestinal contents), wall frames (e.g., frames that have passed a wall detector or a classifier and received a "positive" indication), tunnel frames (e.g., frames that have passed a tunnel detector or a classifier and received a "positive" indication), or wrinkle pattern frames (e.g., frames that show a wrinkle star pattern or frames in which the folded intestinal wall is distributed in a radial way) may be used as frame classification categories. Other categories or classifications may be used. A classifier, such as classifier 615 described in FIG. 6, may be used to classify or categorize each frame.

In some embodiments, as indicated at box 730, the method may optionally include, for example, analyzing the measured property or properties to determine intestinal dysfunction condition. For example, analysis of the measured properties may optionally include determining whether the percentage of contraction frames with wrinkle pattern passes a predetermined value. In another example, analysis of the measured properties may optionally include calculating the mean length of the static frames sequences, and determining whether the length is longer than a predetermined value. In yet another example, the number of contractions per minute may be analyzed to determine if it exceeds a predetermined value. In some embodiments, analysis of the measured properties may optionally include summing a number of values corresponding to the analyzed properties and determining intestinal dysfunction condition based on a weighted average of these values. Other methods of analysis may be used.

Some embodiments may provide diagnosis of intestinal dysfunctions based on analysis of different features in a stream of in vivo images. In some cases, the diagnosis may be based on a predetermined set of properties. Such properties may include, inter alia, static frames, turbid frames, tunnel frames, contractions, and wrinkle pattern level presence. Detection and analysis of other properties may be used in addition to these or instead. In one embodiment, a vector of 21 features may be used to diagnose subjects in intestinal motility dysfunctions.

Static frames may appear when there is no apparent motion or little apparent motion of the in vivo device. A high level of static frames may be considered as an indication of intestinal disease. Related information that may be extracted from such images may include, but is not limited to: percentage of static frames in the image stream, percentage of static frames in parts of the image stream, such as those parts of the stream where turbidity is not present, the mean length of the static sequences and the static level of the stream.

Turbid frames may be frames of an in vivo stream of images that include food pieces or intestinal juices, for example. Related information that may be extracted from such images and used for diagnosis may include, but is not limited to: percentage of turbid frames in the image stream, percentage of turbid frames that are also static frames and static level in parts of the image stream, such as in the parts where the turbidity is not present.

A tunnel is a sequence of frames where the lumen may appear static for a long period of time. The interpretation of tunnel may be that there is no contractile movement. Related information that may be extracted from such images and used for diagnosis may include, but is not limited to: percentage of tunnel frames in a stream of images or in parts of a stream, for example only in images where turbidity is not present, the mean length of the tunnel sequence, and the static level of all tunnel frames.

Analysis of intestinal contractions may be useful for diagnosing different intestinal dysfunctions. Intestinal contractions may be occlusive contractions, in which the lumen in the central frame of these contractions is completely closed. Intestinal contractions may be non-occlusive contractions, in which the lumen may not appear closed. Intestinal contractions may be sustained contractions, in which the lumen may be continuously closed. Related information that may be extracted from such images and used for diagnosis may include, but is not limited to: the number of contractions per minute in the image stream or in parts of the image stream, such as parts of the stream that the turbid is not present, and the percentage of contractions that are non-occlusive.

Analysis of wrinkle pattern level presence may be useful for diagnosing different intestinal dysfunctions. Wrinkle star pattern may be an omnipresent characteristic of the sustained contractions. Such pattern may indicate strong edges of the folded intestinal wall, distributed in a radial way around the intestinal lumen. Wrinkle detection may be used in order to identify such patterns, or to determine the level of wrinkle presence in frames. Related information may be extracted from images that have been identified as including a certain level of wrinkle patterns and may be used for diagnosis. Such information may include, but is not limited to: the percentage of frames with wrinkles in an image stream, the percentage of frames without turbid where the wrinkle star pattern appears, the mean length of the wrinkle sequences, the percentage of frames with a high level of wrinkle presence, the percentage of contractions with wrinkles.

Some embodiments may be utilized, for example, to selectively provide automatic or semi-automatic detection of in-vivo images (or frames of an in-vivo image stream), corresponding to contraction(s) and/or contractile activity. Some embodiments, for example, may allow a physician to selectively view and/or rapidly access in-vivo images that correspond to contraction(s), and/or correspond to certain contractile activity (e.g., for diagnosis purposes, to locate or determine a dysfunction in contractile activity, or the like). Some embodiments, for example, may allow shortening of viewing time required by a physician for diagnosis, and/or shortening of time required by a physician to access and/or selectively view in-vivo images that correspond to contraction(s) and/or to contractile activity. Some embodiments, for example, may allow a selective display (or other presentation) of a portion (e.g., a relatively small portion, or multiple small portions) of an in-vivo image stream, which corresponds to contraction(s) and/or to contractile activity. Some embodiments, for example, may allow a physician to determine a portion-of-interest of an in-vivo image stream which the physician may examine, e.g., to detect a portion of an in-vivo image stream which corresponds to contraction(s) and/or contraction activity, for example, for further inspection by the physician. Some embodiments, for example, may allow to "skip" (e.g., by avoiding to display, by fast-forwarding, or the like) one or more portions of an in-vivo image stream based on contractile activity information, e.g., portion(s) that correspond to contractions and/or to contractile activity of interest, portion(s) that do not correspond to contractions and/or to contractile activity of interest, portions that correspond to existence of contractions and/or contractile activity, portions that correspond to absence of contractions and/or contractile activity, or the like. Some embodiments, for example, may allow a physician to concentrate or "focus" his examination of an in-vivo image stream on a portion-of-interest, e.g., based on contraction(s) information and/or other contractile activity information that correspond to the portion-of-interest. Embodiments or the invention may provide various other benefits and/or advantages.

Some embodiments of the invention may include, for example, an in-vivo imaging device having multiple imagers or image sensors, e.g., two or three imagers. For example, in one embodiment, the in-vivo device may include a first imager having a first field of view, and a second imager having a second field of view. In some embodiments, the multiple imagers may face different directions, e.g., at an angle of approximately 45 degrees, at an angle of approximately 90 degrees, at an angle of approximately 180 degrees, or the like.

In some embodiments, the in-vivo device having multiple imagers may be used for collection of data which may be used for generating or analyzing contractile activity information. For example, multiple imagers of the in-vivo device may acquire images, which may be used for analysis, thereby allowing determinations with regard to contractions or contractile activity. In one embodiment, acquired data may be accumulated from multiple imagers; in another embodiment, data acquired from each imager may be processed separately and the results may be compared or further analyzed; other suitable processes may be used.

Devices, systems and methods in accordance with some embodiments of the invention may be used, for example, in conjunction with a device which may be inserted into a human body or swallowed by a person. However, embodiments of the invention are not limited in this regard, and may be used, for example, in conjunction with a device which may be inserted into, or swallowed by, a non-human body or an animal body.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

What is claimed is:

1. A method for analysis of an in-vivo image stream comprising:
   receiving a stream of image frames from an in-vivo imaging device;
   measuring at least a property of each frame of a plurality of image frames of said stream;
   determining frame classifications of each of said plurality of frames based on the measured properties; and
   analyzing the measured properties and the frame classifications to determine the number of contractions in the plurality of image frames.

2. The method according to claim 1 wherein the measured property comprises image intensity value.

3. The method according to claim 2 further comprising:
   calculating an image intensity value for each of a series of in-vivo image frames;
   analyzing a variation of the in-vivo image intensity values corresponding to the series of in-vivo image frames; and
   determining contractile activity information corresponding to one or more in-vivo image frames based on the calculated image intensity values.

4. The method according to claim 3 wherein the series of in-vivo images comprises predetermined number of in-vivo images acquired within a predefined time period.

5. The method according to claim 3 wherein an in-vivo image frame having substantially a highest image intensity value is determined to correspond with a peak of a contraction.

6. The method according to claim 3 further comprising calculating a normalized intensity value substantially for each in-vivo image frame.

7. The method according to claim 1 wherein said classification is selected from a group consisting of: contractile activity frames, static frames, turbid frames, wall frames and tunnel frames.

8. The method according to claim 1 further comprising determining a percentage of contraction frames with a wrinkle pattern.

9. The method according to claim 1 further comprising: calculating a mean length of static frames sequences and determining whether the length is longer than a predetermined value.

10. The method according to claim 1 further comprising analyzing the number of contractions per minute to determine if it exceeds a predetermined value.

11. The method according to claim 1 further comprising providing indication that contractile activity is normal or abnormal.

12. The method according to claim 1 wherein the plurality of in-vivo images is a set of consecutive images of the image stream.

13. The method according to claim 12 wherein the first image of the set corresponds to a cycle of contractile activity.

14. The method according to claim 1 wherein the in vivo imaging device is a swallowable capsule.

* * * * *